US009781949B2

(12) United States Patent
McClements et al.

(10) Patent No.: US 9,781,949 B2
(45) Date of Patent: Oct. 10, 2017

(54) ANTIMICROBIAL DELIVERY SYSTEMS, METHODS OF MANUFACTURE, AND METHODS OF USE THEREOF

(75) Inventors: David Julian McClements, Northampton, MA (US); Lynne McLandsborough, Sunderland, MA (US); Yuhua Chang, Amherst, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 387 days.

(21) Appl. No.: 13/433,661

(22) Filed: Mar. 29, 2012

(65) Prior Publication Data

US 2012/0251699 A1 Oct. 4, 2012

Related U.S. Application Data

(60) Provisional application No. 61/469,903, filed on Mar. 31, 2011.

(51) Int. Cl.
*A23L 3/34* (2006.01)
*A23L 3/3463* (2006.01)
*A01N 37/46* (2006.01)
*A23L 3/3526* (2006.01)

(52) U.S. Cl.
CPC ............ *A23L 3/3463* (2013.01); *A01N 37/46* (2013.01); *A23L 3/3526* (2013.01)

(58) Field of Classification Search
CPC ...... A23L 3/3463; A23L 3/3526; A01N 37/46
USPC ................................ 426/531, 532, 321, 335
See application file for complete search history.

(56) References Cited

U.S. PATENT DOCUMENTS 5,472,952 A 12/1995 Smidt et al.
5,656,591 A * 8/1997 Tomita et al. ................. 514/2.4
5,900,363 A 5/1999 Hiraki et al.
2006/0083830 A1 4/2006 Kemp et al.
2006/0210668 A1 9/2006 Thorsoe et al.
2010/0197810 A1* 8/2010 Hedges ................ A23D 7/0053 514/773
2011/0027394 A1 2/2011 McClements et al.
2011/0046040 A1 2/2011 Mutou et al.
2013/0004617 A1* 1/2013 Zhang ...................... B01J 13/10 426/72

FOREIGN PATENT DOCUMENTS

JP 2004-123630 * 4/2004

OTHER PUBLICATIONS

JP 2004-123630 (Apr. 2004) translation.*

Chang et al.; "Control of Foodborne Pathogens on Ready-to-East Roast Beef Slurry by E-polylysine"; International Journal of Food Microbiology; 141(3); pp. 236-241 (2010).

Geornaras, et al.; "Activity of E-polylysine Against *Escherichia coli* O157:H7"; *Salmonella* Typhimurium, and Listeria Monocytogenes; Journal of Food Science; 70(9); pp. M404-M408; (2005).

Geornaras, et al.; "Antimicrobial Activity of E-Polylysine Against *Escherichia coli* O157:H7, *Salmonella* Typhimurium, and Listeria monocytogenes in Various Food Extracts"; Journal of Food Science; 72(8); pp. M330-M334; (2007).

FDA (2004). Agency Response Letter GRAS Notice No. GRN 000135.

Hiraki, et al.; "Use of ADME Studies to Confirm the Safety of e-polylysine as a Preservative in Food"; Regulatory Toxicology and Pharmacology; 37(2); pp. 328-340; (2003).

Najjar, et al.; "E-Poly-L-lysine and Nisin A Act Synergistically Against Gram-positive Food-borne Pathogens Bacillus Cereus and Listeria Monocytogenes"; Letters in Applied Microbiology; 45(1), pp. 13-18; (2007).

Shih, et al.; "Microbial Synthesis of Poly(e-lysine) and its Various Applications"; Bioresource Technology; 97(9); pp. 1148-1159; (2006).

Shima et al.; "Polylysine Produced by Streptomyces"; Agricultural and Biological Chemistry: 41(9); pp. 1807-1809; (1977).

Shima, et al.; "Antimicrobial Action of Epsilon-Poly-L-Lysine"; Journal of antibiotics; 37(11), pp. 1449-1455; (1984).

Thakur, et al.; "Chemistry and Uses of Pectin—A Review"; Critical Reviews in Food Science and Nutrition; 37(1); pp (1997) 47-73;.

Yamanada, et al; "Mechanism of Epsilon-Poly-L-Lysine Production and Accumulation Revealed by Identification and Analysis of an epsilon-Poly-L-Lysine-Degrading Enzyme"; Applied and Environmental Microbiology; 76(17); pp. 5669-5675; (2010).

Yoshida, et al.; "E-Poly-L-lysine: Microbial Production, Biodegradation and Application Potential"; Appl Microbiol Biotechnol; 62; pp. 21-26; (2003).

Asker et al.; "Formation and Stabilization of Antimicrobial Delivery Systems Based on Electrostatic Complexes of Catitonic-Non-iconic Mixed Micelles and Anionic Polysaccharides"; J. Agri. Food Chem; 59; pp. 1041-1049; (2011).

Chang et al.; "Cationic Antimicrobial (e-Polysine)—Anionic Polysaccharide (Pectin) Interactions: Influence of Polymer Charge on Physical Stability and Antimicrobial Efficacy"; Journal of Agricultural and Food Chemistry; 60; pp. 1837-1844; (2012).

International Search Report and Written Opinion; International Application No. PCT/US2012/031556; International Filing Date Mar. 30, 2012; Date of Mailing Sep. 6, 2012; 13 pages.

Wu et al.; "Assessment of Oligogalacturonide from Citrus Pectin as a Potential Antibacterial Agent Against Foodborne Pathogens"; J. Good Sci.; 79(8); pp. 1541-1544; (2014) Abstract-only 1 page.

* cited by examiner

*Primary Examiner* — Leslie Wong
(74) *Attorney, Agent, or Firm* — Cantor Colburn LLP

(57) ABSTRACT

Disclosed herein is an antimicrobial delivery system comprising an electrostatic complex comprising cationic biopolymer and an anionic biopolymer, wherein the antimicrobial delivery system has antimicrobial activity in a comestible.

9 Claims, 12 Drawing Sheets

Mass ratio of pectin-to-ε-PL

| $R_{GA-PL}$ | 0 | 5 | 10 | 15 | 20 | 25 | 30 | 50 |
|---|---|---|---|---|---|---|---|---|

ANTIMICROBIAL DELIVERY SYSTEMS, METHODS OF MANUFACTURE, AND METHODS OF USE THEREOF

CROSS-REFERENCE TO RELATED APPLICATIONS

This application claims the benefit of U.S. Provisional Patent Application Ser. No. 61/469,903, filed Mar. 31, 2011, which is incorporated by reference herein in its entirety.

STATEMENT REGARDING FEDERALLY SPONSORED RESEARCH & DEVELOPMENT

The U.S. Government has certain rights in this invention pursuant to United States Department of Agriculture, Agriculture and Food Research Initiative, NIFA Grant (Nanoscale Science and Nanotechnology to Ensure Safe Food: Proposal Number: 2010-03459).

BACKGROUND

ϵ-Polylysine (ϵ-PL) is a cationic antimicrobial agent having strong antimicrobial activity. Because ϵ-PL is highly effective against a broad spectrum of food pathogens and spoilage organisms, and it has great potential for utilization in food and beverage products. Further, based on absorption, distribution, metabolism, excretion, and toxicity (ADMET) studies, ϵ-PL has been shown to be safe for human consumption. For this reason, it has been approved as generally recognized as safe (GRAS) within the United States for certain food applications.

Despite its high antimicrobial activity, nontoxicity, water-solubility, and good thermal stability use of ϵ-PL in foods and beverages (comestibles) is currently limited, because it tends to cause product turbidity and/or to form sediments. For example, the addition of as little as 1 ppm (part per million) ϵ-PL to a commercial green tea beverage can result in the formation of visible precipitates after a short storage time (24 hours). Therefore, the use of ϵ-PL as an antimicrobial in comestibles is limited despite its efficacy and safety.

There is thus a need for improvements in the delivery of ϵ-PL to comestibles. It would be advantageous if such delivery could provide high antimicrobial efficacy, together with one or more of long-term antimicrobial efficacy, good physicochemical stability in a comestible, food or beverage, and good aggregation stability in a comestible.

SUMMARY

Disclosed herein is an antimicrobial delivery system comprising an electrostatic complex comprising a cationic biopolymer and an anionic biopolymer. In an advantageous feature, the antimicrobial delivery system has antimicrobial activity in a comestible.

In another embodiment, a composition comprises a comestible and the antimicrobial delivery system in an antimicrobially-effective amount.

Further disclosed is a method for manufacturing an antimicrobial delivery system, comprising forming an electrostatic complex comprising an antimicrobially effective amount of a cationic biopolymer and an anionic biopolymer.

Also disclosed is a method for manufacturing a comestible, comprising combining the comestible and the above-described antimicrobial delivery system in an amount effective to have antimicrobial activity in the comestible.

A method of inhibiting microbial growth in a comestible comprises storing a comestible comprising an antimicrobially effective amount of the above-described electrostatic complex for a length of time effective to prevent microbial growth in the comestible.

The invention is further illustrated by the following Drawings, Detailed Description, and Examples.

DETAILED DESCRIPTION

Figure 1:
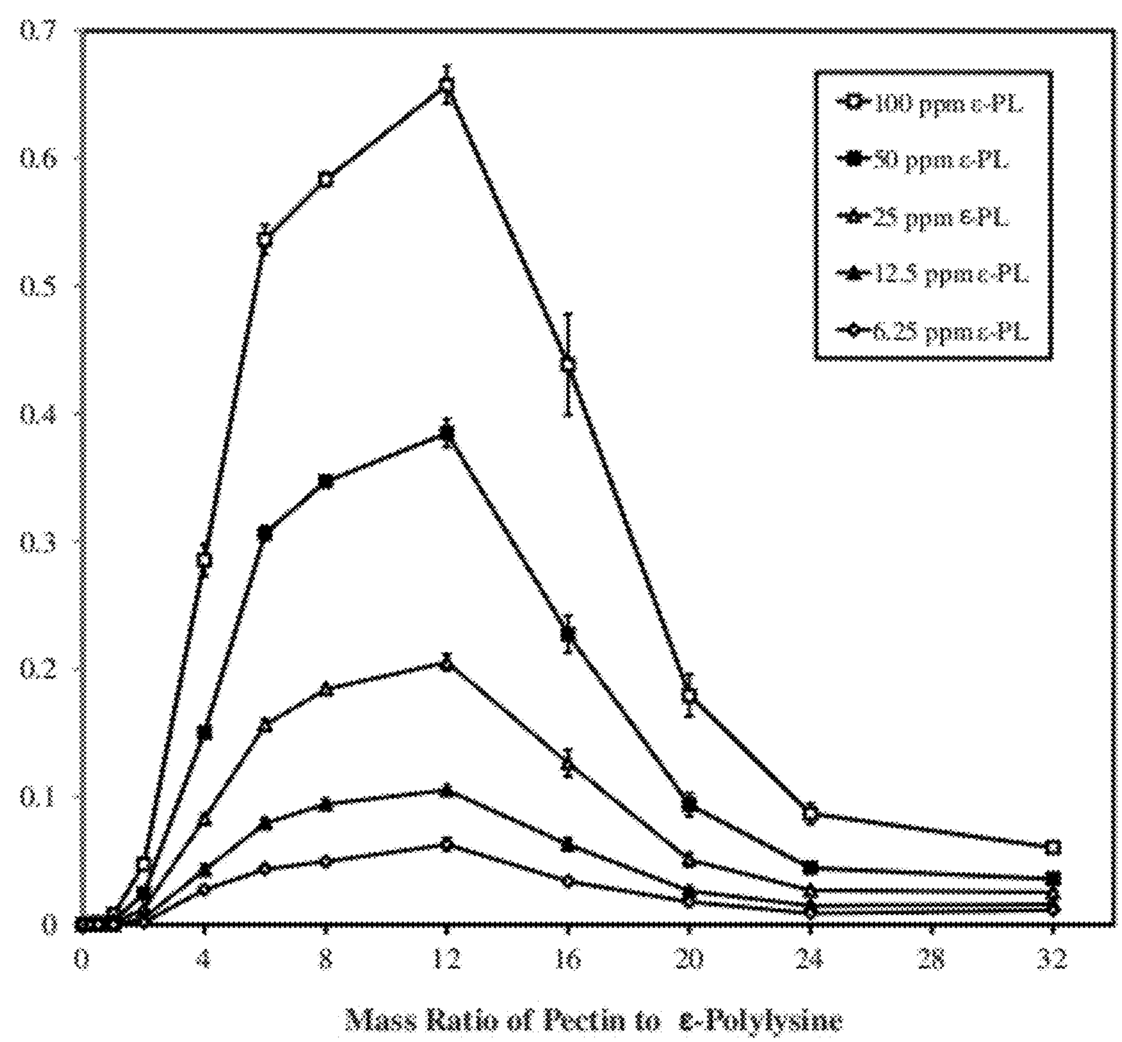
FIG. 1 shows the dependence of turbidity (at 600 nm) of ϵ-PL-pectin complexes aqueous solutions on mass ratios of pectin-to-ϵ-PL for different concentrations of ϵ-PL.

The present inventors have developed novel antimicrobial delivery systems comprising electrostatic complexes of cationic and anionic biopolymers. The electrical characteristics of these complexes can be controlled by varying the nature and ratio of the biopolymers used to form them. In a particularly advantageous feature, the delivery systems overcome the drawbacks associated with the use of cationic biopolymers in comestibles, particularly in liquids, in that they are stable complexes that maintain their antimicrobial efficacy over time. Thus, the antimicrobial delivery systems have good physicochemical stability while still maintaining appreciable antimicrobial efficacy when used in foods or beverages.

Suitable cationic biopolymers include ϵ-PL, chitosan, chitosan sulfate, and combinations thereof. An exemplary cationic biopolymer is ϵ-PL. ϵ-PL is an antimicrobial agent having high antimicrobial activity, low or negligible toxicity, water-solubility, and good thermal stability. Without being bound by theory, it is believed that its use in comestibles is currently limited at least in part because of its tendency to associate with anionic substances, thereby increasing product turbidity or forming sediments. ϵ-PL is cationic when the environmental pH is lower than its isoelectric point (pI=about 9.0) because of the primary amine groups along its backbone. Again without being bound by theory, the antimicrobial activity of ϵ-PL is thought to function by absorbing onto negatively-charged cell surfaces of microorganisms through electrostatic interactions. On the other hand, the cationic nature of ϵ-PL may form undesirable precipitates when used in some comestibles if it interacts with anionic components within the comestible, leading to an increase in product cloudiness or to the formation of sediments. ϵ-PL may also complex with human saliva causing astringency. Therefore, both the beneficial attributes (antimicrobial) and detrimental attributes (precipitate formation, astringency) of ϵ-PL are likely to depend on its electrical characteristics. This invention provides the means to control the electrical attributes of ϵ-PL to reach a balance between high antimicrobial efficacy and good aggregation stability.

Accordingly, disclosed herein is an antimicrobial delivery system comprising an electrostatic complex comprising a cationic polymer such as ϵ-polylysine and an anionic biopolymer, wherein the antimicrobial delivery system has antimicrobial activity in a comestible.

ϵ-PL is a polymer comprising L-lysine monomers linked together by isopeptide bonds between ϵ-amino and α-carboxyl groups. The ϵ-PL for use in the electrostatic complex is selected based on its ability to form a stable electrostatic complex with the selected anionic biopolymer, its antimicrobial activity, availability, cost, and like considerations. The ϵ-PL can have 5 to 100 lysine units, specifically 10 to 50 lysine units, more specifically 20 to 40 lysine units. The ϵ-PL can be a homopolymer, or a small number (e.g., 1 to 20, 1 to 10, or 1 to 5) of other units (e.g., other amino acids) can be present. In an embodiment, such units do not significantly adversely affect the advantageous properties of the ϵ-PL or the electrostatic complex formed therefrom, for example toxicity, water-solubility, thermal stability, or antimicrobial activity.

The ϵ-PL is complexed with an anionic biopolymer (which is defined below) to form the delivery system. The anionic polymer is selected based in its ability to form a stable electrostatic complex with the ϵ-PL, low toxicity, availability, cost, and like considerations. The anionic biopolymer can be branched or linear. Suitable anionic biopolymers include, but are not limited to, polysaccharides, polypeptides, polynucleotides, or a combination comprising at least one of the foregoing. In an embodiment, the anionic biopolymers are food grade biopolymers. Suitable polysaccharide biopolymers include, but are not limited to, food grade ionic or ionizable polysaccharides such as pectins, alginic acids, alginates, gum arabic, gum acacia, carageenans, xanthans, agars, tree gums and exudates thereof, guar gum, gellan gum, tragacanth gum, karaya gum, locust bean gum, lignin, and/or combinations thereof. Suitable polypeptide biopolymers include, but are not limited to, food grade ionic or ionizable proteins such as whey, casein, soy, egg, plant, meat and fish proteins, ovalbumins, glycoproteins, mucoproteins, phosphoproteins, serum albumins and collagens. The protein can be selected on the basis of its amino acid residues (e.g., polar or charged amino acids such as lysine, arginine, aspartic acid, glutamic acid, etc.) to optimize overall net charge, interaction with ϵ-PL, and/or resultant ϵ-PL-biopolymer complex stability. Suitable polynucleotides include nucleic acids such as DNA and RNA. The food grade biopolymer may alternatively be selected from modified polymers such as modified starch, modified celluloses, carboxymethyl cellulose, carboxymethyl dextran or lignin sulfonates.

In an embodiment the anionic biopolymer is pectin, which is an anionic polysaccharide that is readily available and widely used within the food and beverage industries. Pectin is a heteropolysaccharide of partially esterified α-1,4 linked D-galacturonides, containing varying amounts of covalently attached rhamnose and branches of L-arabinose, D-galactose, D-xylose, and L-rhamnose. It has carboxylic acid side groups that are negatively charged across a wide range of pH values ($pK_a$=about 3.5). Pectin is isolated from plant primary cell walls. Pectin can be isolated from a variety of plants including citrus fruit, sugar beets, potatoes, and pears. Isolated pectin has a molecular weight of about 60 to about 130,000 g/mol, varying with origin and extraction conditions.

In an embodiment, the pectin has a high degree of esterification. In another embodiment, the pectin has a low degree of esterification. As used herein, a high degree of esterification refers to a pectin having 50% or more of its carboxyl side groups esterified while a low degree of esterification refers to a pectin having 50% or fewer of its carboxyl side groups esterified. The carboxyl side groups can be esterified with methanol to provide methoxyl groups. An exemplary pectin is high methoxyl pectin (HMP). In an embodiment, some carboxyl groups are acetylated. In an embodiment, the pectin is amidated wherein one of the galacturonic acids is converted with ammonia to carboxylic acid amide.

In an embodiment, the anionic biopolymer is gum arabic, which is also known as acacia gum, chaar gund, char goond, or meska, is a natural gum made of hardened sap taken from two species of the acacia tree; *Acacia senegal* and *Acacia seyal*. The gum is harvested commercially from wild trees throughout the Sahel from Senegal and Sudan to Somalia. Gum arabic is a complex mixture of polysaccharides and glycoproteins that is readily available and widely used within the food and beverage industries.

The electrostatic complex may be formed by known methods, for example by combining an aqueous solution comprising the ϵ-PL and an aqueous solution comprising the anionic biopolymer, or by adding the ϵ-PL or the anionic biopolymer to an solution comprising the anionic biopolymer or the ϵ-PL respectively. The electrostatic complex thus formed may be concentrated, isolated, or directly combined with the comestible. In some embodiments, the electrostatic complex is formed in situ, that is, in the presence of at least one component of the comestible. Other components may be present in the solutions, for example an organic solvent miscible with water (e.g., ethanol), a pH adjusting agent, a stabilizer, a preservative, another comestible ingredient, or a combination thereof.

The mass ratio of the anionic polymer to ϵ-PL ($R_{AP-PL}$), such as for example, pectin-to-ϵ-PL ($R_{P-PL}$) and gum arabic-to-ϵ-PL ($R_{GA-PL}$) affects the overall electrical characteristics of the delivery systems, which in turn influences their aggregation stability and antimicrobial efficacy. The electrical charge on the complexes changes from positive to negative with increasing $R_{AP-PL}$. Unexpectedly, soluble complexes or dispersible colloids were formed at low and at high $R_{AP-PL}$ levels, but insoluble complexes were formed at intermediate $R_{AP-PL}$ levels. The effective concentration and/or mass ratio of the anionic biopolymer and ϵ-PL will depend on the biopolymer used as well as the solution in which the complexes are formed. In an embodiment, the mass ratio of anionic biopolymer to ϵ-PL in the antimicrobial delivery system is about 1 to about 40. Specifically, the mass ratio of anionic biopolymer to ϵ-PL in the antimicrobial delivery system is about 2 to about 20, more specifically about 4 to about 10. In an embodiment, the mass ratio of anionic biopolymer to ϵ-PL in the antimicrobial delivery system is about 8 to about 20.

The antimicrobial delivery system comprising an electrostatic complex can further comprise one or more additional components, for example the water in which the complex is formed, a stabilizer, a preservative, or other component to be added to the comestible.

In an embodiment, the antimicrobial delivery system comprises an electrostatic complex that has a minimum inhibitory concentration (MIC) of less than about 10 ppm. Specifically, the electrostatic complex has a MIC of less than about 6 ppm, more specifically, less than about 3 ppm, even more specifically, less than about 2 ppm.

In use, the cationic ϵ-PL forms an electrostatic complex with the anionic biopolymer in the comestible. The comestible is selected based in part on the comestible having an appropriate environment (e.g., pH, temperature, ionic strength) such that the ϵ-PL and the anionic biopolymer have net electrical charges sufficient to form and/or maintain the electrostatic complex. In a specific embodiment the comestible is a liquid. In another embodiment, the comestible is a clear liquid. Clear liquids may have, for example, an $OD_{600}$ of less than or equal to 0.3 $cm^{-1}$ as measured in a one centimeter (cm) path length optical cell, specifically less than or equal to 0.2 $cm^{-1}$, more specifically less than or equal to 0.15 $cm^{-1}$, and even more specifically less than or equal to 0.1 $cm^{-1}$.

The antimicrobial delivery system may be combined with the comestible by any means, for example mixing. As stated above, the antimicrobial delivery system can be pre-formed, or formed by addition to a solution comprising at least one component of the comestible. The combination may then be further processed, for example combined with other components or packaged for storage or shipping.

In an embodiment, the antimicrobial delivery system is present in the comestible an amount effective to kill or inhibit the growth of greater than or equal to about 90% of microorganisms in the comestible when combined with the comestible. Specifically, the antimicrobial delivery system is present in an amount effective to kill or inhibit the growth of greater than or equal to about 95%, more specifically, greater than or equal to about 99%, and even more specifically, greater than or equal to about 99.9%, of microorganisms in the comestible when combined with the comestible.

Effective amounts of the antimicrobial deliver system will depend on the particular ϵ-PL and anionic polymer used, the anionic polymer to ϵ-PL ratio, comestible used, and the type of microorganism present. In an embodiment, ϵ-PL is present in an amount up to about 200 ppm by weight based on the weight parts of the comestible, specifically up to about 100 ppm, more specifically up to about 50 ppm, and even more specifically up to about 25 ppm. Specifically, ϵ-PL is present in an amount from about 1 ppm to about 10 ppm by weight based on the weight parts of the comestible.

In an embodiment, the anionic biopolymer is present in an amount up to about 200 ppm, specifically up to about 100 ppm, more specifically up to about 50 ppm, and even more specifically about 1 to about 25 ppm by weight based on the weight parts of the comestible.

In an embodiment, ϵ-PL is present in an amount of about 10 ppm and the anionic biopolymer is present in an amount of about 20 ppm to about 200 ppm each by weight based on the weight parts of the comestible. Specifically in an embodiment, the antimicrobial delivery systems comprise an ϵ-PL-pectin complex, for example about 10 ppm ϵ-PL and about 20 to about 200 ppm pectin, each by weight based on the weight parts of the comestible. In another embodiment, the antimicrobial delivery systems comprise about 100 ppm ϵ-PL and about 200 to about 2000 ppm pectin, each by weight based on the weight parts of the comestible.

The antimicrobial delivery systems are stable to aggregation. Stable to aggregation, as used herein, refers to antimicrobial delivery systems that when present in a solution, yield solutions that have low turbidity, and do not form visible sediments or precipitates. In an embodiment, the solution containing the antimicrobial delivery system has low turbidity and no visible sediments or precipitates after storage for up to about six months, specifically up to about three months, more specifically up to about one month, and even more specifically up to about two weeks. The solution may be stored at ambient temperature (about 23° C.) or refrigerated (about 4° C.). Low turbidity, as used herein, refers to a solution having an $OD_{600}$ of less than or equal to 0.3 as measured in a one centimeter (cm) path length optical cell, specifically less than or equal to 0.2, more specifically less than or equal to 0.15, and even more specifically less than or equal to 0.1. The control solution, without the antimicrobial delivery systems, will serve as a reference or blank to set its $OD_{600}$ at zero. Visible sediments or precipitate, as used herein refers to sediments or precipitates in a solution that are visible to the unaided human eye.

While this disclosure has been directed to ϵ-PL, other cationic polymers may be used to form the electrostatic complex, including synthetic polymers and biopolymers. Suitable cationic biopolymers include, but are not limited to, chitosan and chitosan sulfate. The cationic polymers have a net charge when combined with a comestible. In an embodiment, the cationic polymer can have a net charge over a wide range of pH values, for example about 2 to about 8

The following examples are provided for illustrative proposes and are not intended to limit the scope of the invention as claimed herein. Any variations in the exemplified compositions and methods that occur to the skilled artisan, are intended to fall within the scope of the present invention.

EXAMPLES

Fabrication of ϵ-Polylysine-Polysaccharide Complexes as Antimicrobial Delivery Systems Materials and Methods Cationic antimicrobial ϵ-polylysine (PuraQ Xtend FX50P) is commercially available from Purac America (Lincolnshire, Ill.). High methoxyl pectin (HMP) with a degree of esterification (DE) of approximately 71% (Pectin 1400) is commercially available from TIC Gums (Belcamp, Md.). Gum arabic is commercially available from Sigma-Aldrich (St. Louis, Mo.). Yeast media, Difco Malt Extract Agar (MEA) and Malt Extract Broth (MEB), are commercially from Becton Dickinson (Sparks, Md.). Lipton® Green Tea is an exemplary commercial tea beverage. An exemplary model beverage (20% apple juice broth) was prepared according to the methods provided by Pepsico, which contained 20% pure apple juice (Motts' aseptic filled brickpak) and had a total sugar content of 11° Brix, with pH adjusted at 3.5 by malic acid.

Stock solutions of ϵ-polylysine and high methoxyl pectin (HMP, degree of esterification (DE) value 71%) are prepared by dispersing appropriate amounts of powdered ingredients into double distilled water, followed by pH adjustment to pH 3.5.

Appropriate volumes of ϵ-polylysine, pectin stock solutions, and water (adjusted to pH 3.5) are mixed to create complexes having a range pectin-to-PL mass ratios ($R_{P-PL}$). The mass ratios $R_{P-PL}$ range from about 0 to about 32. The antimicrobial delivery systems comprise the formed ϵ-PL-pectin complexes. Appropriate amounts of complex solutions are applied into food and beverage systems.

Micro-electrophoresis (ME) and Turbidity Measurements. Micro-electrophoresis and turbidity measurements are used to provide information about the electrical charge and aggregation state of ϵ-PL-pectin complexes, respectively.

Appropriate volumes of ϵ-polylysine, pectin stock solutions, and sterile water (adjusted to pH 3.5) are mixed to create complexes with different pectin-to-ϵ-PL mass ratios ($R_{P-PL}$). The concentration of ϵ-PL is fixed at 100 ppm, and the pectin concentrations are varied ($R_{P-PL}$=0.25, 0.5, 1, 2, 4, 6, 8, 12, 16, 20, 24, and 32). The resulting ϵ-PL-pectin complex solutions are mixed thoroughly and stored for 24 hours prior to analysis.

Stock solutions of □-polylysine (1%, pH 3.5) and gum arabic (2.0%, pH 3.5) are prepared in double distilled water. The stock solutions are filter sterilized (0.45-mm pore size; Corning Incorporated, Corning, N.Y.) and kept refrigerated until used. Appropriate volume of □-polylysine, gum arabic solutions and sterile water (adjusted to pH 3.5) are mixed to create complexes of different gum arabic:PL ratios. The concentration of □-polylysine (PL) is fixed at 200 ppm, and the gum arabic concentrations are varied (gum arabic:PL ratios 0, 5, 10, 15, 20, 25, 30, 40, 50).

The electrical charge (ζ-potential) of the particles in the solutions are measured using a particle electrophoresis instrument (Zetasizer Nano-ZS, model ZEN3600, Malvern Instruments, Worchester, U.K.). The ζ-potential is calculated from measurements of the electrophoretic mobility of particles in an applied oscillating electric field using laser doppler velocimetry. All measurements are conducted on at least two freshly prepared samples and repeated three times per sample.

The optical turbidity (at 600 nm) of the solutions is measured using a UV-visible spectrophotometer (Ultraspec 2000, Pharmacia Biotech) at ambient temperature (approximately 23° C.). The samples are contained within 1 cm path length optical cells, and distilled water is used as a control. Turbidity measurements are carried out on at least two freshly prepared samples.

Yeast Strains. Two strains of acid resistant spoilage yeasts, *Zygosaccharomyces bailli* (ZB) and *Saccharomyces cerevisiae* (SC), are used to examine the antimicrobial effects of ϵ-PL-polysaccharide complexes. Both strains are obtained from the Pepsico R&D Culture Collection (Valhalla, N.Y.). Yeast cultures are kept frozen at −70° C. in 25% glycerol. The yeast strains are refreshed on MEA plates before the following tests of MICs. A single yeast colony from the plate is then inoculated into 10 ml of MEB broth, which is adjusted to pH 3.5 by citrate buffer (10 mM in final media). The culture is incubated at 25° C. under mild agitation (150 rpm in a rotary shaker) for about 2 days until the optical density (turbidity) at 600 nm ($OD_{600}$) is about 1.0. As a guideline, an $OD_{600}$ of 1.0 corresponds to approximately $5\times10^6$ CFU/ml (Colony Forming Units/ml) for cultures of yeast strains.

Determination of the Minimum Inhibitory Concentration of ϵ-Polylysine-Pectin Complexes. The ϵ-PL-pectin complexes are prepared as described previously. The antimicrobial effectiveness of ϵ-PL-pectin complexes is determined by calculating the Minimum Inhibitory Concentration (MIC) using a microbroth dilution assay against the two yeast strains. Briefly, sterile microtiter plates are inoculated with ϵ-PL-pectin complex solutions (100 μA of varying concentrations, and an equal volume of inoculated 2×MEB broth (pre-adjusted to pH 3.5 using 20 mM citrate buffer) is added and mixed thoroughly. The resulting 1×MEB media contains 10 mM citrate buffer. The target yeast cell inoculation level is around 5×104 CFU/ml in the final 1×MEB medium. For each microtiter plate, a specific ϵ-PL-pectin complex is tested that has a specific ϵ-PL concentration (100 ppm to 1.6 ppm) and pectin-to-ϵ-PL ratio (0, 0.25, 0.5, 1, 2, 4, 6, 8, 12, 16, 24, or 32). Plates are incubated at 25° C. for 6 days, and the MICs are assessed visually as the lowest concentration of ϵ-PL showing complete inhibition of growth. All MIC experiments are repeated twice with freshly prepared materials.

Determination of the antimicrobial efficacy of varying complexes in the model apple juice beverage. The effectiveness of antimicrobial of each □-Polylysine-Gum Arabic complex is determined by testing the Minimum Inhibitory Concentrations (MIC) using a microbroth dilution assay against the two yeast strains. Briefly, sterile microtiter plates are inoculated with □-Polylysine-Gum Arabic complex solutions (approximately 100 microliters) with varying concentrations, and an equal volume of inoculated 2× model apple juice (pH 3.5) is added (the resulting solution composed of 1× model apple juice medium). The target inoculation level is about $10^4$ or $10^2$ CFU/ml. Plates are incubated at 25° C. for 7 days, and the MICs are assayed visually as the lowest concentration showing complete growth inhibition.

Influence of ϵ-PL-pectin complexes on stability of tea beverages. 250 ppm of ϵ-polylysine is combined with different ratios of pectin ($R_{P-PL}$=0, 0.25, 0.5, 1, 2, 4, 6, 8, 12, 16, 20, 24, and 32; pH 3.5), vortexed to mix evenly, and let stand for at least 1 hour to let the complexes develop completely. A non-food grade antimicrobial (400 ppm sodium azide) is added to the green tea samples to ensure that the influence of the ϵ-PL-pectin complexes on the physical appearance of the products is not influenced by any microbial growth. Appropriate amounts of PL-pectin solutions are added to 40 ml of green tea (pH 3.6), to obtain a final ϵ-PL concentration of 10 ppm. After vortexing for about 1 minute to mix thoroughly, the resulting solutions are stored at room temperature. The turbidity of the resulting solutions over time is measured at 600 nm using a spectrophotometer in 1 cm path length optical cells using distilled water as a blank. The formation of precipitates or sediments is also recorded by visual observation and digital photography.

Stability of □-PL-Gum Arabic complexes in a model beverage. 2 mL of the □-PL-gum arabic solutions are added to 40 ml of a model beverage (20% apple juice broth), to make final □-PL concentrations to be 10 ppm. After votexing for about 1 minute to mix thoroughly, the resulting solutions are stored in a dark area at room temperature for 15 days. The turbidity of the resulting solutions is measured at 600 nm over time using a spectrophotometer using 1 cm path length optical cells with distilled water as a blank. The formation of precipitates is also recorded by a digital camera.

Example 1: Aggregation Characteristics of ϵ-Polylysine-Pectin Complexes

The aggregation characteristics of ϵ-PL-pectin complexes is characterized using turbidity measurements and visual observation. ϵ-PL molecules (about 100 to about 6.25 ppm) are complexed with pectin molecules with varying mass ratios of pectin-to-ϵ-PL (about 0.25 to about 32) at pH 3.5. Small soluble complexes do not scatter light strongly and so lead to the formation of clear solutions with low turbidity, whereas large insoluble complexes scatter light strongly and so lead to the formation of cloudy colloidal suspensions with high turbidity and possibly sedimentation. A series of solutions are prepared containing fixed amounts of ϵ-PL (100, 50, 25, 12.5, and 6.25 ppm) and varying amounts of pectin ($R_{P\text{-}PL}$ from 0 to 32). The turbidity and visual appearance of the solutions (pH 3.5) are then measured. For the turbidity measurements, the samples are mixed thoroughly prior to analysis to ensure that any complexes are evenly distributed throughout the whole sample. For visual observation, the samples are stored at ambient temperature for 24 hours to determine the stability of the complexes to gravitational separation.

As shown in FIG. 1, the turbidity ($OD_{600}$) of ϵ-PL-pectin complex solutions containing 100 ppm of ϵ-PL increased slowly when $R_{P\text{-}PL}$ is increased from 0 to 2, but the values are very low ($<0.05\ cm^{-1}$). This suggests that the size of the ϵ-PL-pectin complexes formed is so small that they do not scatter light strongly. The turbidity then increases steeply when $R_{P\text{-}PL}$ increases from 2 to 12, suggesting that large insoluble complexes are formed that scattered light strongly. Finally, the turbidity progressively decreases as $R_{P\text{-}PL}$ increases further, suggesting that the size of the complexes decreases.

Figure 2:
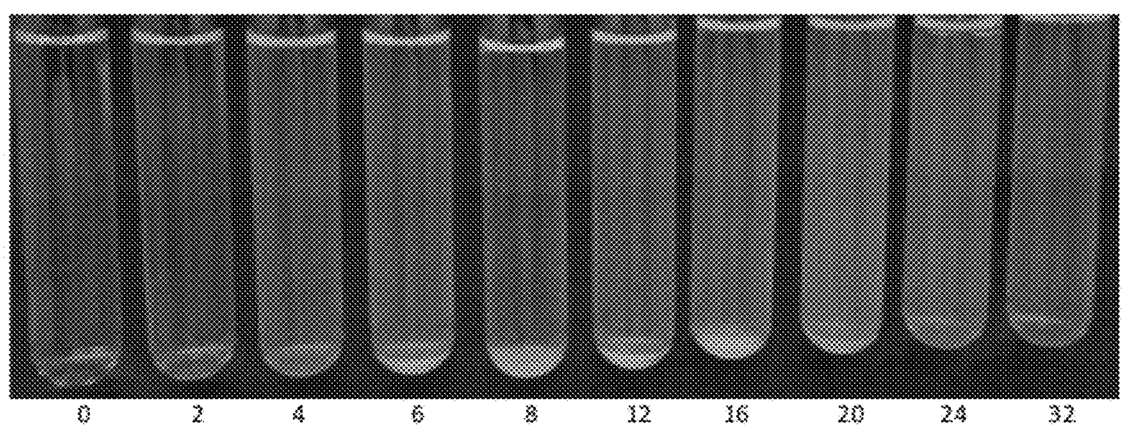
FIG. 2 shows the appearance of aqueous solutions containing ϵ-PL-pectin complexes (pH 3.5) comprising 100 ppm of ϵ-PL and pectin with varying mass ratios of pectin-to-ϵ-PL.

As shown in FIG. 2, visual observation of the solutions indicated that they are transparent at low pectin concentrations ($R_{P\text{-}PL}\leq 2$), form turbid colloidal suspensions or white sediments at intermediate pectin concentrations ($4\leq R_{P\text{-}PL}\leq 16$), and form relatively stable colloidal dispersions at high pectin concentrations ($R_{P\text{-}PL}\geq 20$).

Figure 3:
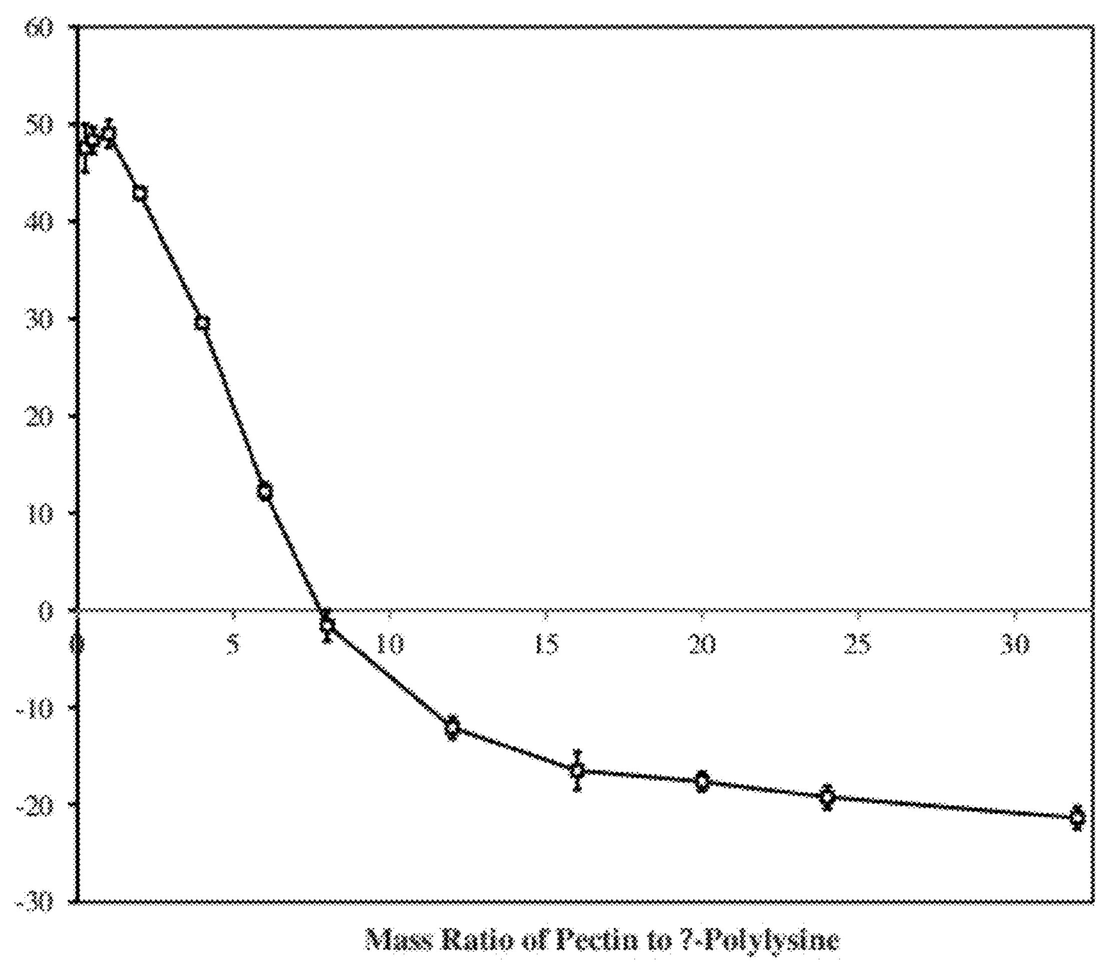
FIG. 3 is a graph depicting the dependence of the ζ-potential of ϵ-PL-pectin complexes solutions on the mass ratio of pectin-to-ϵ-PL for 100 ppm of ϵ-PL (pH 3.5)

Similarly, at lower levels of ϵ-PL, increasing pectin concentration initially increases the turbidity until it reached a maximum value, and then the turbidity decreases. (FIG. 1) However, the magnitudes of the turbidity values decreases as the concentration of ϵ-PL in the systems decreases. This may be due to a dilution effect, i.e., fewer particles present to scatter light. At ≤12.5 ppm ϵ-PL, all the ϵ-PL-pectin complex solutions remain transparent and stable to aggregation (maximum $OD_{600}<0.1\ cm^{-1}$) (FIG. 1), irrespective of pectin concentration. This result suggests that complexes containing low ϵ-PL concentrations may be suitable for application within clear acidic beverages Example 2: Electrical Characteristics of ϵ-Polylysine-Pectin Complexes FIG. 3 shows the electrical characteristics (ζ-potential) of ϵ-PL-pectin complexes (100 ppm ϵ-PL; pH 3.5) as measured by micro-electrophoresis. As shown in FIG. 3, the ζ-potential of ϵ-PL-pectin complexes solutions is dependent on the mass ratio of pectin-to-ϵ-PL for 100 ppm of ϵ-PL (pH 3.5). In ϵ-PL-pectin complexes having low concentrations of pectin ($R_{P\text{-}PL}\leq 1$), the charge of the resulting complexes is highly positive (ζ≈+48 mV). As the pectin concentration increases, the ζ-potential changes from positive to negative (FIG. 3). Thus, ϵ-PL-pectin complexes are positively charged at low $R_{P\text{-}PL}$, but negatively charged at high $R_{P\text{-}PL}$, with charge neutralization occurring at $R_{P\text{-}PL}\sim 8$. Without being bound by theory, electrostatic repulsion may play an important role in maintaining the stability of these ϵ-PL-pectin complexes. The complexes are stable when their net charges are either highly positive or highly negative; otherwise they become turbid and/or precipitate and form sediments at the bottom of the tubes (FIG. 2).

Example 3: Antifungal Efficacy of ϵ-Polylysine-Pectin Complexes

The antimicrobial effects of different ϵ-PL-pectin complexes are measured by their minimum inhibitory concentration (MIC) in a nutrient MEB medium (pH 3.5), against two yeast strains: *Zygosaccharomyces bailli* (ZB) and *Saccharomyces cerevisiae* (SC). These two yeasts are selected as target organisms because they are acid resistant and may cause spoilage in acidic beverages.

Figure 4:
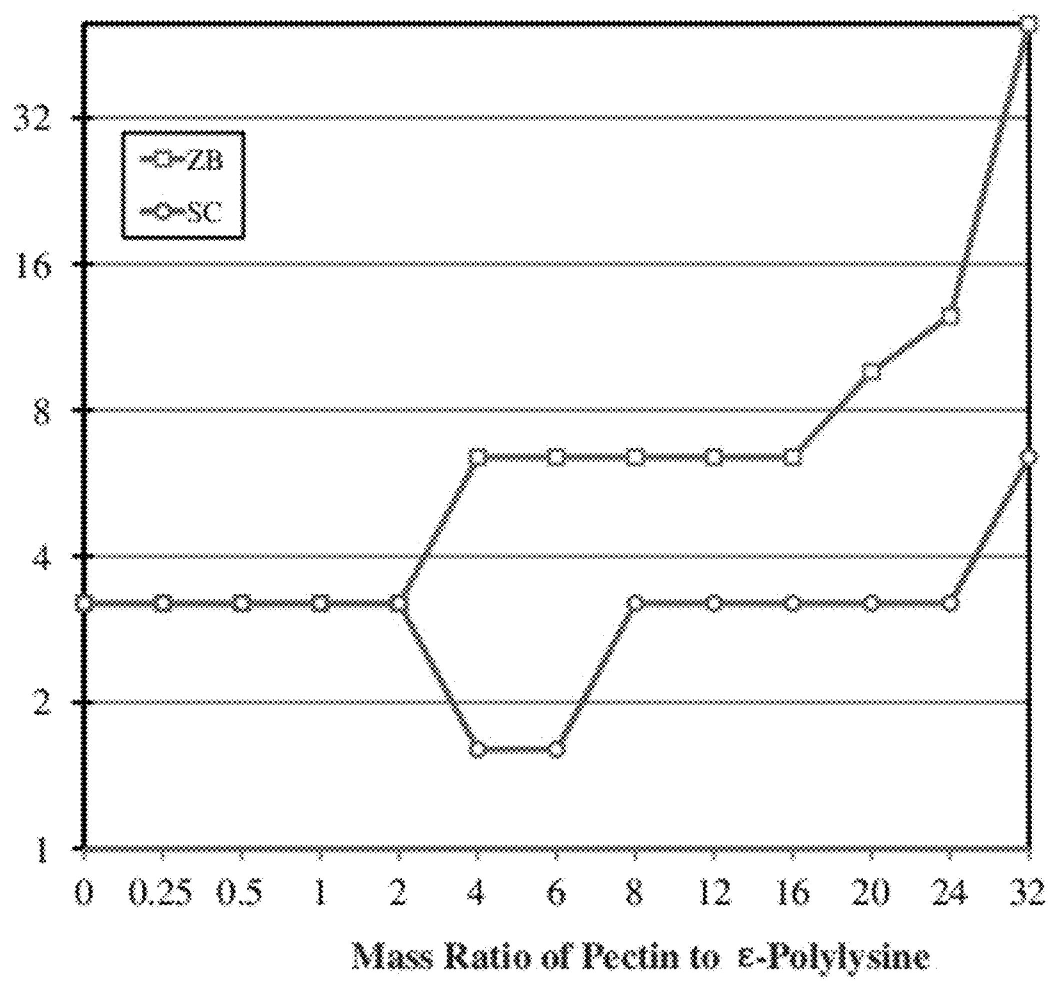
FIG. 4 is a graph depicting the dependence of the minimal inhibitory concentration (MIC) of ϵ-PL-pectin complexes with varying mass ratios of pectin-to-ϵ-PL.

As shown in FIG. 4, in the absence of pectin, ϵ-PL is highly effective at inhibiting the growth of both yeast strains, with a MIC of 3.2 ppm. Without being bound by theory, the antimicrobial efficacy of cationic polymers has been attributed to their ability to interact with and disrupt anionic cell membranes, thereby leading to cell leakage or lysis. Generally, the antimicrobial efficacy of ϵ-PL decreases with increasing levels of pectin, as indicated by increasing MIC with increasing $R_{P\text{-}PL}$ (FIG. 4). For ZB, the MIC of ϵ-PL increased from 3.2 to 6.4 ppm when ϵ-PL is complexed with between 4 and 16 times of pectin. The MIC of ϵ-PL further increases to 9.6, 12.5 and 50 ppm when ϵ-PL is complexed with 20, 24 and 32 times of pectin, respectively. For SC, the MIC of ϵ-PL increases from 3.2 to 6.4 ppm when ϵ-PL is complexed with 32 times of pectin.

The decrease in antimicrobial activity of the ϵ-PL-pectin complexes may be attributed to the reduction in the positive change and the increase in the negative charge on the complexes having increased pectin levels (FIG. 3). Accordingly, one would expect that the electrostatic attraction between the ϵ-PL-pectin complexes and negatively charged yeast cell surfaces would be reduced and the electrostatic repulsion would be increased.

Despite this expectation, the complexes unexpectedly still have relatively high antifungal efficacy even when their net charge is neutral or negative as shown in FIGS. 3 and 4. Without being bound by theory, this unexpected result could be due to: (i) the cationic ϵ-PL molecules are at least partially released from the complexes due to competition between the anionic pectin and anionic yeast cell surfaces; or (ii) even though the complexes as a whole are negative, there are some localized parts that are positively charged, which could be attracted to the negatively charged yeast cell surfaces.

In general, increasing the level of pectin tends to reduce the antifungal efficacy of ϵ-PL for both ZB and SC; however, this effect is yeast specific. SC is much less sensitive to increased levels of pectin. For SC, the MIC of ϵ-PL did not increase when ϵ-PL is complexed with ≤24 times of pectin. Even when ϵ-PL is complexed with 32 times of pectin, its MIC only increased from 3.2 to 6.4 ppm. Without being bound by theory, this phenomenon could result from differences in the surface charges of the two yeasts. The morphology of the two yeasts were observed using differential interference contrast (DIC) optical microscopy, and found that their shape and size are very similar to each other. However, their surface charges are quite different: −12.3±2.2 mV (SC) versus −7.8±2.6 mV (ZB). The cell surface of SC had a higher negative charge, and may therefore have been able to attract the ϵ-PL-pectin complexes more strongly. It is also possible that the surface micro-structures differ between the two yeasts, resulting in different steric repulsion.

FIG. 4 shows another unexpected result: ϵ-PL-pectin complexes have better antifungal activity than pure ϵ-PL against SC at $R_{P-PL}=4$ or 6. The physicochemical origin of this effect is currently unknown. At these $R_{P-PL}$ values the net charge on the complexes is slightly positive (FIG. 3), which suggests that they could still be electrostatically attracted to the anionic surfaces of the yeast cells.

Although the antimicrobial efficacy of ϵ-PL decreases with increasing amounts of pectin, the ϵ-PL-pectin complexes are still highly effective against both yeast strains tested. When complexed with ≤16 times of pectin, relatively low levels of ϵ-PL (6.4 ppm) are still able to inhibit the growth of both yeasts, suggesting that these complexes could be utilized in food and beverage systems. The net charge of ϵ-PL-pectin complexes is negative for $R_{P-PL}>8$, while their antimicrobial efficacies are still strong for $R_{P-PL}$ between 8 and 20 i.e., MIC<10 ppm for both ZB and SC. This result suggests that ϵ-PL-pectin complexes with $8<R_{P-PL}<20$ may reduce ingredient precipitation and astringency (because they are anionic), while still maintaining antimicrobial activity.

Example 4: Influence of ϵ-PL-Pectin Complexes in a Green Tea Beverage Model

A series of ϵ-PL-pectin complexes with different $R_{P-PL}$ are incorporated into a commercial green tea beverage to test their impact on product turbidity and sediment formation. ϵ-PL molecules (10 ppm) are complexed with different levels of pectin. The optical densities are measured after 2 weeks storage at room temperature.

Figure 5:
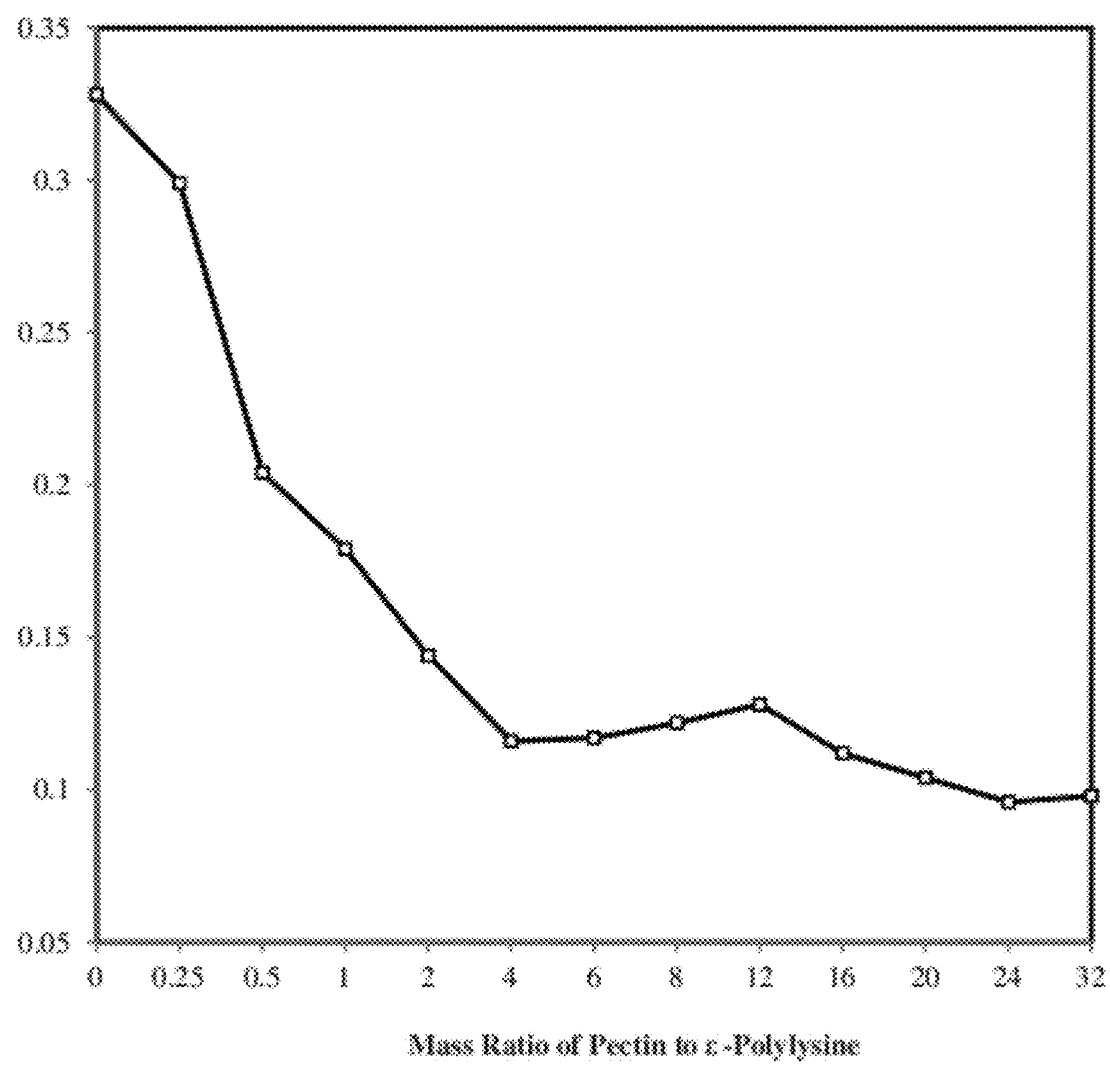
FIG. 5 shows a graph depicting the dependence of the turbidity (at 600 nanometers) of green tea beverage on the presence of ϵ-PL-pectin complexes with varying mass ratios of pectin-to-ϵ-PL (about 0 to about 32)
Figure 6:
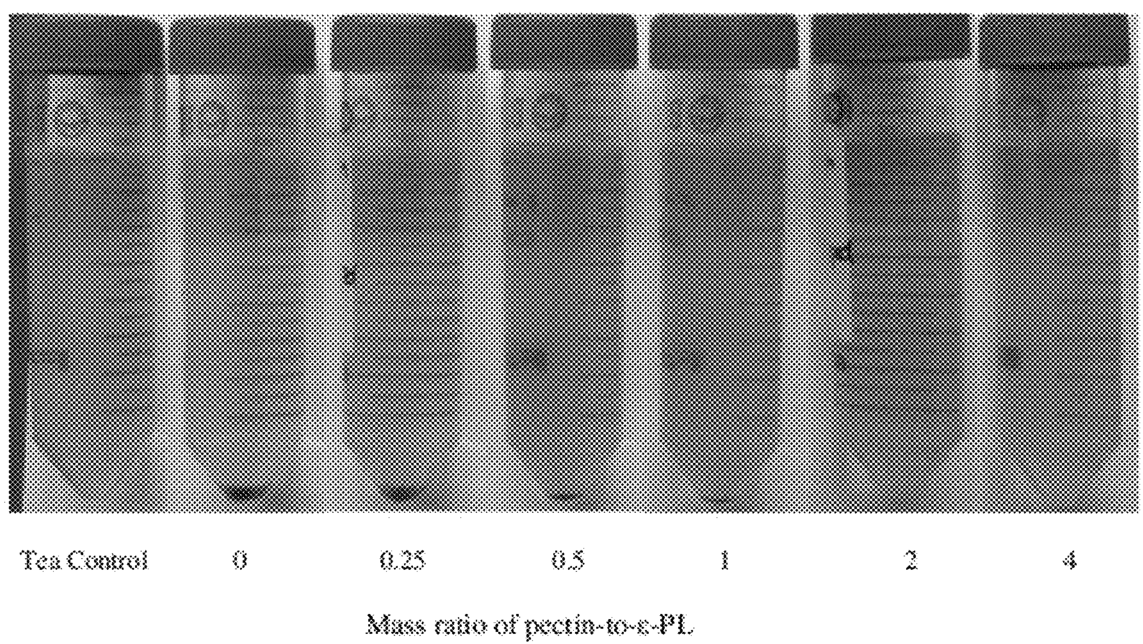
FIG. 6 shows the appearance of a commercial green tea beverage containing ϵ-PL-pectin complexes (pH 3.5) comprising 10 ppm of ϵ-PL and varying mass ratios of pectin-to-ϵ-PL.

As shown in FIGS. 5 and 6, there is an increase in turbidity and sediment formation in the tea samples when 10 ppm ϵ-PL is added. FIG. 6 shows several tea samples ($R_{P-PL}$ 0, 0.25, 0.5, and 1) having a brown sediment at the bottom of the tubes. This suggests that there are anionic components within the tea that could interact with the cationic polylysine and form large aggregates. Indeed, as little as 1 ppm ϵ-PL causes the formation of visible precipitates in the green tea beverage after storage for only four days. Accordingly, polylysine could not be directly applied into these products. However, the use of ϵ-PL-pectin complexes results in appreciable improvements to the stability of the products to cloudiness and sedimentation. There is an appreciable decrease in the turbidity of the samples and a reduction in the amount of sediment as the amount of pectin in the complexes increases. For $R_{P-PL}\geq 4$, the turbidity remains low, the samples appear clear, and no sediment is visible after 2 weeks storage (FIGS. 5 and 6).

These results indicate that polylysine can be incorporated into tea beverages, provided it is first complexed with a sufficient amount of an anionic biopolymer. The ϵ-PL-pectin complexes therefore have a weaker tendency to interact with any anionic components within the green tea than pure ϵ-PL, presumably because there are fewer cationic groups present to react.

As shown in FIG. 4, the higher the levels of pectin present in the ϵ-PL-pectin complexes, the better the stability to cloudiness or precipitation. On the other hand, in terms of antimicrobial effects, the lower the levels of pectin present in the complexes, the higher the antimicrobial efficacy. These results suggest that ϵ-PL-pectin complexes should be specifically designed to obtain an optimum balance between these two opposing effects. In an embodiment, ϵ-PL-pectin complexes comprising 10 ppm ϵ-PL and $R_{P-PL}$ from about 2 to about 20 have good physical stability in a green tea model, while still demonstrating appreciable antifungal efficacy against two acid resistant yeasts in MEB medium.

Example 5: Influence of ϵ-PL-Gum Arabic Complexes in an Apple Juice Beverage Model Electrostatic complexes are formed between cationic ϵ-PL and anionic gum arabic, and their aggregation stability, electrical charge, and antifungal efficacy are tested. The nature of the complexes formed depended on the mass ratio of Gum Arabic-to-ϵ-PL ($R_{GA-PL}$), since this determined their electrical characteristics, aggregation stability, and antimicrobial efficacy. The electrical charge on the complexes went from positive to negative with increasing $R_{GA-PL}$, with the point of zero charge being around $R_{GA-PL}$ of about 15.

Figure 7:
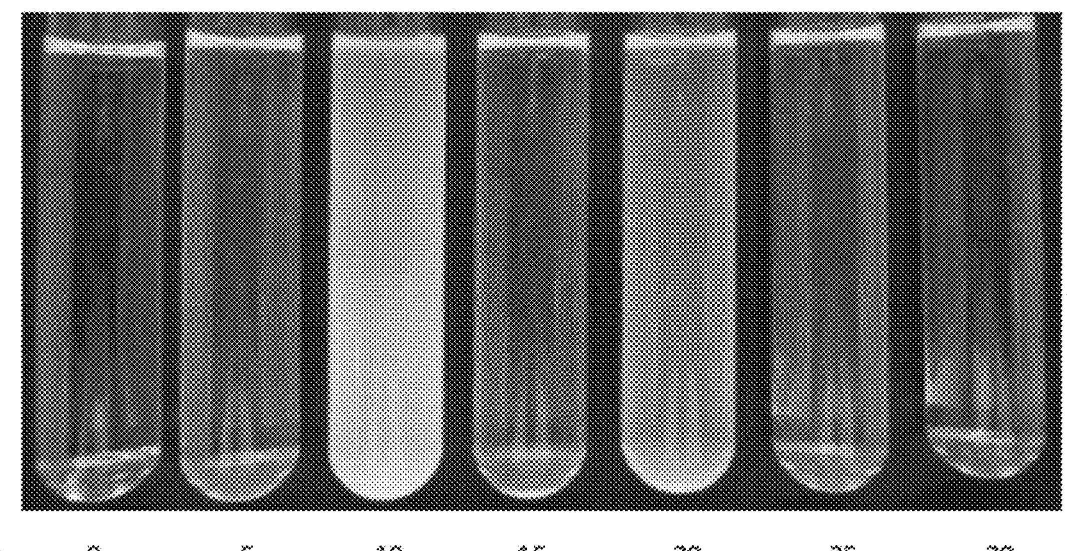
FIG. 7 shows the appearance of a solution containing □-PL-Gum Arabic complexes at different mass ratios of gum arabic to □-PL ($R_{GA-PL}$)

As shown in FIG. 7, soluble ϵ-PL-Gum Arabic complexes are formed at low and high $R_{GA-PL}$ levels, but insoluble complexes are formed at intermediate levels ($R_{GA-PL}$ between about 5 and about 25). The complexes are formed from 200 ppm ϵ-PL and gum arabic of varying ratios (from 5 to 30).

Figure 8:
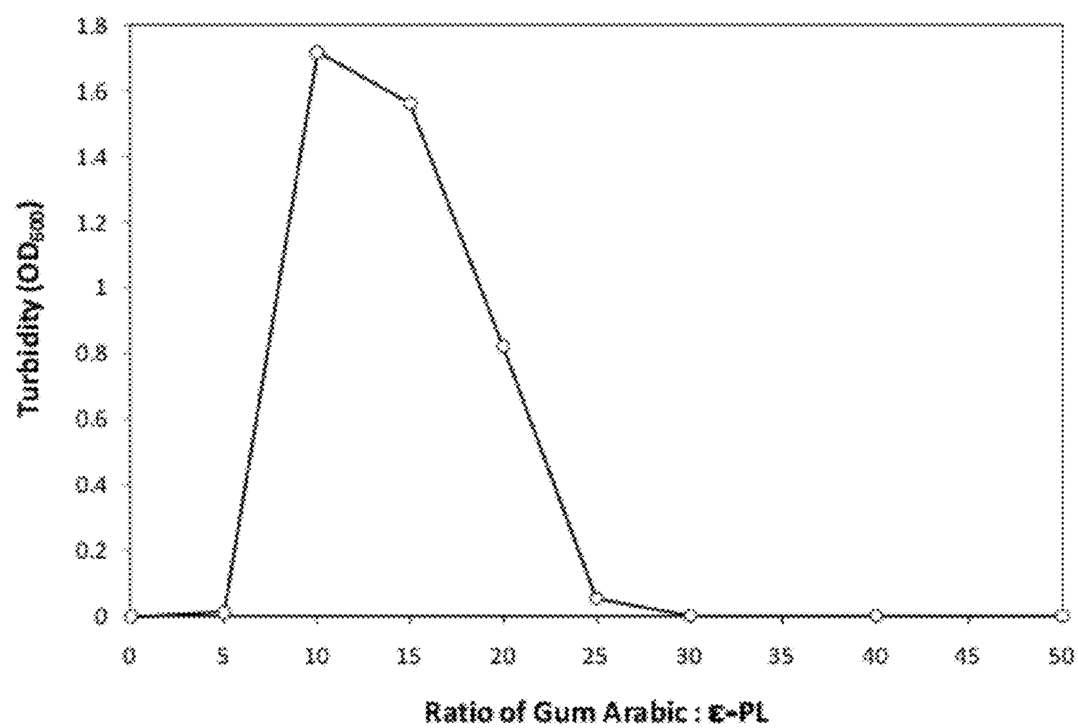
FIG. 8 shows the dependence of the turbidities of □-PL-Gum Arabic complexes in solution on the mass ratio of gum arabic to □-PL.
Figure 9:
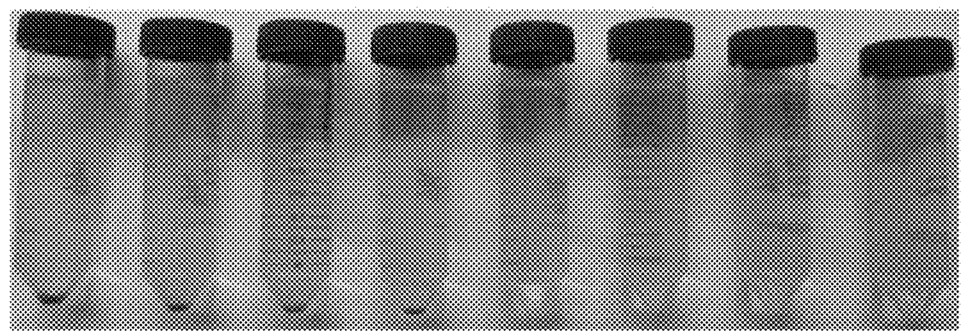
FIG. 9 shows the turbidity of a 20% apple juice model beverage supplemented with different □-PL-Gum Arabic complexes.
Figure 10:
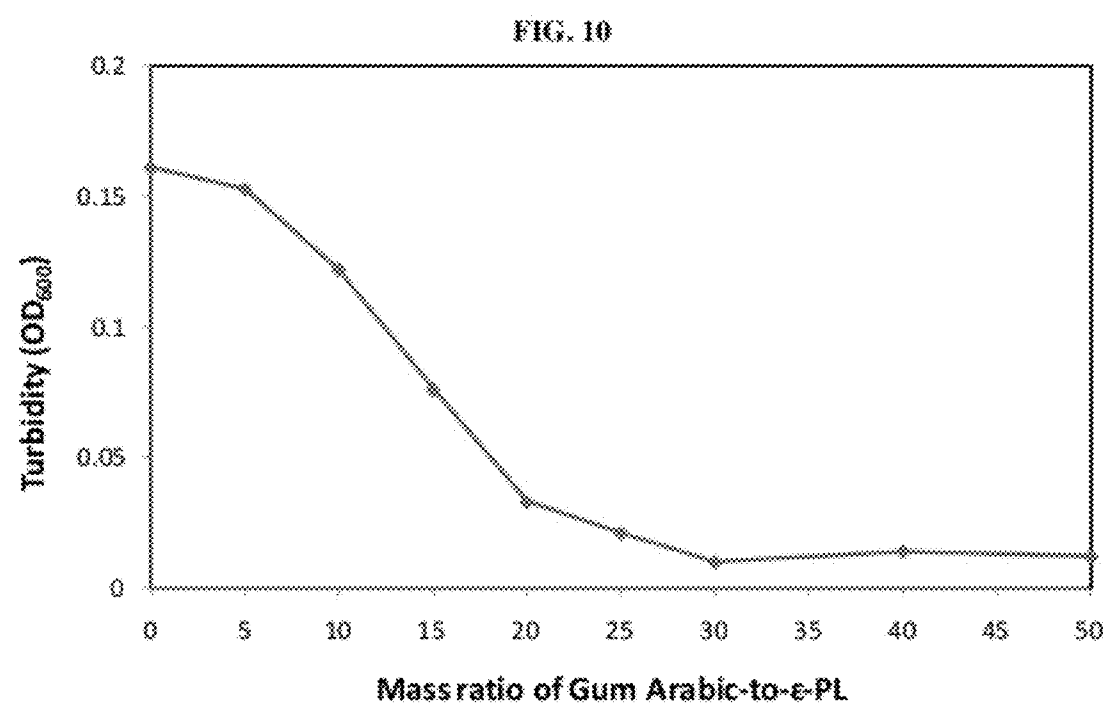
FIG. 10 shows the dependence of the turbidities of □-PL-Gum Arabic complexes in the 20% apple juice model beverage on the mass ratio of gum arabic to □-PL.

Certain ϵ-PL-Gum Arabic complexes (10 micrograms/ml ϵ-PL; $R_{GA-PL}$ greater than or equal to 20) can be incorporated into a model beverage (20% apple juice broth) without adversely affecting the appearance or physical stability of the model beverage. FIG. 8 shows the dependence of the turbidities of □-PL-Gum Arabic complexes (pH 3.5) on the mass ratio of gum arabic to □-PL. The complexes are formed from 200 ppm ϵ-PL and gum arabic of varying ratios from 0 to 50. FIG. 9 shows the visual appearance of the 20% apple juice model beverage supplemented with different ϵ-PL-Gum Arabic complexes. The final beverages contained 10 ppm ϵ-PL and gum arabic of varying ratios from 0 to 50. Photos are taken after storage for 15 days at room temperature. There was no visible sediment when $R_{GA-PL}$ was greater or equal to 20. FIG. 10 shows the turbidity of the 20% apple juice model beverage supplemented with different ϵ-PL-Gum Arabic complexes. Optical densities (OD600) are measured after storage for 15 days at room temperature.

Figure 11:
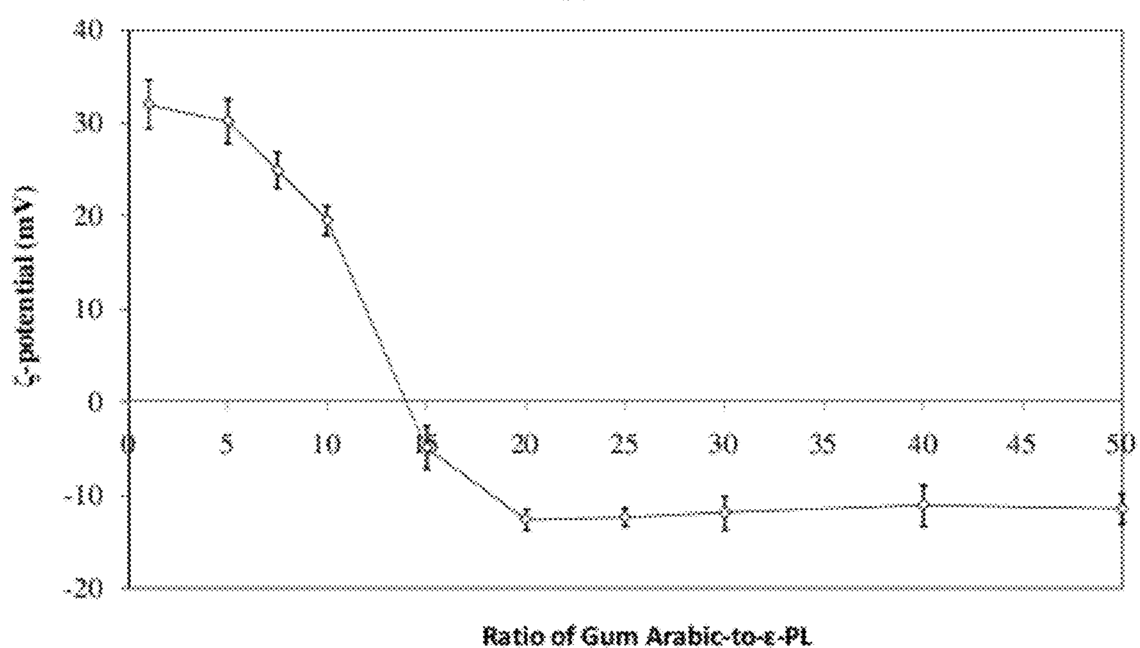
FIG. 11 shows the dependence of the ζ-potential of □-PL-Gum Arabic complexes on the mass ratio of gum arabic to □-PL.

FIG. 11 shows the dependence of the ζ-potential of □-PL-Gum Arabic complexes (pH 3.5) on the mass ratio of gum arabic to □-PL. The complexes are formed from 200 ppm ϵ-PL and gum arabic of varying ratios from 0 to 50. The electrical charge on the complexes went from positive to negative with increasing $R_{GA-PL}$, with the point of zero charge being approximately $R_{GA-PL}$ of 15.

Figure 12:
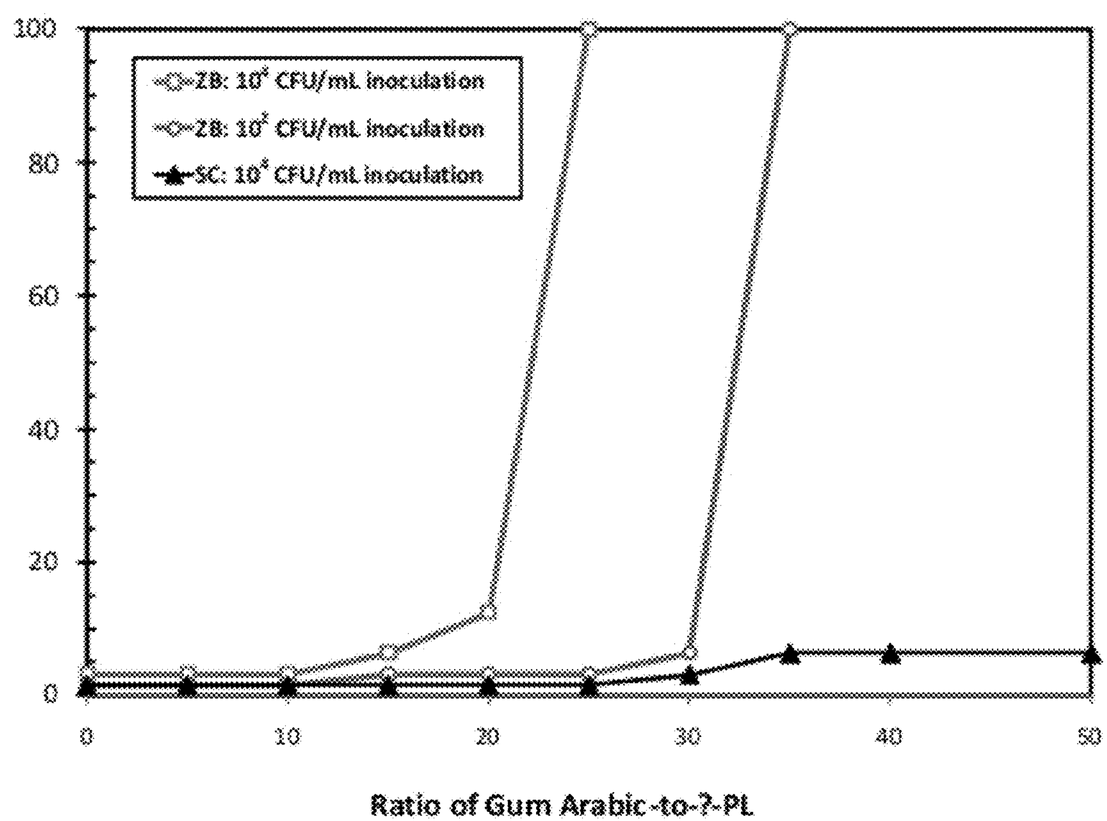
FIG. 12 shows the dependence of the antimicrobial efficacy of □-PL-Gum Arabic complexes in the 20% apple juice model beverage on the mass ratio of gum arabic to □-PL.

FIG. 12 shows the dependence of antimicrobial efficacy of □-PL-Gum Arabic complexes (pH 3.5) on the mass ratios of Gum Arabic to □-PL (from 0 to 50). The 20% apple juice model beverage is supplemented with ϵ-PL-Gum Arabic complexes of varying concentrations. The yeast cells (ZB or SC) are inoculated at the levels of $10^4$ CFU/mL or $10^2$ CFU/ml as indicated. The minimal inhibitory concentration of □-PL is assayed to determine the antimicrobial efficacy of varying □-PL-Gum Arabic complexes. In general, the antimicrobial efficacy of □-PL decreased when levels of gum arabic increased.

When $R_{GA-PL}$ is less than or equal to 20, the □-PL-Gum Arabic complexes has appreciable antimicrobial efficacy (MIC equals less than about 12.5 ppm) against ZB when the initial inoculation is at high levels ($10^4$ CFU/ml). If ZB is inoculated at relatively low levels ($10^2$ CFU/ml), the □-PL-Gum Arabic complexes had appreciate antimicrobial efficacy (MIC is less than or equal to 6.4 ppm) when $R_{GA-PL}$ is less than or equal to 30. SC is much less sensitive to the increased level of gum arabic as compared with ZB, as revealed by the fact that even when $R_{GA-PL}$ increased to 50, the MIC of the □-PL-Gum Arabic complexes only slightly increased to 6.4 ppm at high inoculation levels ($10^4$ CFU/ml).

These results indicate that some □-PL-Gum Arabic complexes, for example, $R_{GA-PL}$=20, could be applied into the model apple juice beverage to inhibit the growth of ZB at high levels ($10^4$ CFU/ml) and maintain good stability because the complexes did cause sediment formation or increased turbidity. These results further indicate that when ZB levels were relatively low, for example, $10^2$ CFU/ml, (which more closely approximates real-world beverage processing conditions under good quality controls), a greater range of □-PL-Gum Arabic complexes, for example, $R_{GA-PL}$, of about 20 to about 30, could be applied into the model apple juice beverage, with good stability and significant antimicrobial activity.

Unless defined otherwise, technical and scientific terms used herein have the same meaning as is commonly understood by one of skill. Compounds are described using standard nomenclature.

The term "comestible" as used herein means a substance or composition comprising more than one substance for human or animal consumption. Comestibles includes foods and beverages in all forms, including solids, semi-solids, and liquids. The comestible may undergo further processing prior to consumption. An exemplary comestible is a clear liquid, i.e., a clear beverage.

The term "beverage" as used herein means any drinkable liquid or semi-liquid, including for example flavored water, soft drinks, fruit drinks, coffee-based drinks, tea-based drinks, juice-based drinks, milk-based drinks, gel drinks, carbonated or non-carbonated drinks, alcoholic or non-alcoholic drinks.

As used herein, the term "food grade" means that up to specified amounts of the particular compounds can be ingested by a human or animal without generally causing deleterious health effects and/or have a GRAS (generally recognized as safe) status.

As used herein, the term "charged" or "ionic" means that the polymer has a net electrical charge when combined with the comestible in which it is used.

As used herein, "biopolymer" refers to a polymer that is ingestible. A biopolymer may have a uniform composition or may be a combination of different polymers. Biopolymers include homopolymers, copolymers, or a combination thereof. A biopolymer may be a polymer derived from a natural source, such as a living organism, or it may be synthetic or semi-synthetic. Biopolymers include, for example, polysaccharides, polypeptides, polynucleotides, and combinations thereof.

The term "antimicrobial" refers to an ability to kill or inhibit the growth of microorganisms (including, without limitation, viruses, bacteria, yeast, fungi, protozoa, etc.), or to attenuate the severity of a microbial infection. Exemplary microorganisms include acid resistant spoilage yeasts *Zygosaccharomyces bailli* and *Saccharomyces cerevisiae.*

The terms "first," "second," and the like, "primary," "secondary," and the like, as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The endpoints of all ranges directed to the same component or property are inclusive of the endpoints is independently combinable, and includes all intermediate ranges.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An antimicrobial delivery system for a comestible, the delivery system comprising:

an electrostatic complex comprising a cationic biopolymer, wherein the cationic biopolymer is ϵ-polylysine, and an anionic biopolymer, wherein the anionic biopolymer is gum arabic wherein anionic biopolymer and cationic biopolymer are present in a mass ratio of anionic biopolymer to cationic biopolymer of 4 to 40, wherein the electrostatic complex exhibits a minimum inhibitory concentration of less than 10 ppm against *Zygosaccharomyces bailli* or *Saccharomyces cerevisiae* in the comestible, wherein a solution containing the electrostatic complex has low turbidity measured as an $OD_{600}$ of less than or equal to 0.3 as measured in a one centimeter (cm) path length optical cell, and wherein a solution containing the electrostatic complex exhibits no visible sediment or precipitates upon storage at room temperature for two weeks, when the solution includes the ϵ-polylysine at a concentration of 1 to 200 ppm.

2. The antimicrobial delivery system of claim 1, wherein the comestible is a liquid.

3. The antimicrobial delivery system of claim 1, wherein the antimicrobial activity is effective to kill or inhibit the growth of greater than or equal to about 90.0% of the microorganisms in the comestible.

4. A comestible composition comprising a comestible component; and an electrostatic complex comprising a cationic biopolymer, wherein the cationic biopolymer is a ϵ-polylysine, and an anionic biopolymer, wherein the anionic biopolymer is gum arabic, wherein anionic biopolymer and cationic biopolymer are present in a mass ratio of anionic biopolymer to cationic biopolymer of about 4 to about 40, wherein the electrostatic complex exhibits a minimum inhibitory concentration of less than 10 ppm against *Zygosaccharomyces bailli* or *Saccharomyces cerevisiae* in the comestible composition, wherein a solution containing the electrostatic complex has low turbidity measured as an $OD_{600}$ of less than or equal to 0.3 as measured in a one centimeter (cm) path length optical cell, and wherein a solution containing the electrostatic complex exhibits no visible sediment or precipitates upon storage at room temperature for two weeks, when the solution includes the ϵ-polylysine at a concentration of 1 to 200 ppm.

5. The comestible composition of claim 4, wherein no precipitates or sediments are observable in the comestible by the unaided eye after combination with the electrostatic complex.

6. A method for manufacturing an antimicrobial delivery system comprising:

combining a cationic biopolymer and an anionic biopolymer in an aqueous solution to form an electrostatic complex having antimicrobial activity in a comestible, wherein the cationic biopolymer is a ϵ-polylysine, and wherein the anionic biopolymer is gum arabic, wherein anionic biopolymer and cationic biopolymer are present in a mass ratio of anionic biopolymer to cationic biopolymer of 4 to 40, wherein the electrostatic complex exhibits a minimum inhibitory concentration of less than 10 ppm against *Zygosaccharomyces bailli* or *Saccharomyces cerevisiae* in the comestible composition, wherein a solution containing the electrostatic complex has low turbidity measured as an $OD_{600}$ of less than or equal to 0.3 as measured in a one centimeter (cm) path length optical cell, and wherein a solution containing the electrostatic complex exhibits no visible sediment or precipitates upon storage at room temperature for two weeks, when the solution includes the ϵ-polylysine at a concentration of 1 to 200 ppm.

7. A method for inhibiting microbial growth in a comestible, comprising combining an antimicrobially effective amount of an electrostatic complex comprising a cationic biopolymer and an anionic biopolymer with the comestible, wherein the cationic biopolymer is a ϵ-polylysine, and wherein the anionic biopolymer is gum arabic, wherein anionic biopolymer and cationic biopolymer are present in a mass ratio of anionic biopolymer to cationic biopolymer of 4 to 40, wherein the electrostatic complex exhibits a minimum inhibitory concentration of less than 10 ppm against *Zygosaccharomyces bailli* or *Saccharomyces cerevisiae* in the comestible composition, wherein a solution containing the electrostatic complex has low turbidity measured as an $OD_{600}$ of less than or equal to 0.3 as measured in a one centimeter (cm) path length optical cell, and wherein a solution containing the electrostatic complex exhibits no visible sediment or precipitates upon storage at room temperature for two weeks, when the solution includes the ϵ-polylysine at a concentration of 1 to 200 ppm.

8. The comestible of claim 4, wherein the comestible is a liquid.

9. The method of claim 7, wherein the comestible is a liquid.

* * * * *